(12) United States Patent
Belrhiti et al.

(10) Patent No.: US 11,867,632 B2
(45) Date of Patent: Jan. 9, 2024

(54) DEVICE FOR CHARACTERISING A LIQUID MATERIAL

(71) Applicant: COMMISSARIAT À L'ÉNERGIE ATOMIQUE ET AUX ÉNERGIES ALTERNATIVES, Paris (FR)

(72) Inventors: Younès Belrhiti, Grenoble (FR); Mickaël Albaric, Grenoble (FR); Malek Benmansour, Grenoble (FR); David Pelletier, Grenoble (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 299 days.

(21) Appl. No.: 17/292,603

(22) PCT Filed: Nov. 4, 2019

(86) PCT No.: PCT/FR2019/052594
§ 371 (c)(1),
(2) Date: May 10, 2021

(87) PCT Pub. No.: WO2020/099758
PCT Pub. Date: May 22, 2020

(65) Prior Publication Data
US 2022/0026368 A1    Jan. 27, 2022

(30) Foreign Application Priority Data

Nov. 14, 2018  (FR) ........................................ 1860509

(51) Int. Cl.
*G01N 21/71* (2006.01)
*G01N 33/205* (2019.01)
*B01F 27/1125* (2022.01)

(52) U.S. Cl.
CPC ......... *G01N 21/718* (2013.01); *G01N 33/205* (2019.01); *B01F 27/1125* (2022.01); *G01N 2201/0697* (2013.01)

(58) Field of Classification Search
CPC ............... G01N 21/718; G01N 33/205; G01N 2201/0697; B01F 27/1125
See application file for complete search history.

(56) References Cited

U.S. PATENT DOCUMENTS 4,802,656 A * 2/1989 Hudault ................ C22B 21/064
266/225
2003/0197125 A1    10/2003 De Saro et al.
(Continued)

FOREIGN PATENT DOCUMENTS

CN    108077382 A  *  5/2018  ............... A22C 5/00
EP    1914534 A2    4/2008
(Continued)

OTHER PUBLICATIONS

International Search Report for PCT/FR2019/052594 dated Mar. 18, 2020 and English translation thereof.
(Continued)

*Primary Examiner* — Jamil Ahmed
(74) *Attorney, Agent, or Firm* — Pearne & Gordon LLP

(57) ABSTRACT

A device for characterising at least one liquid material includes an analysis head and a rotating mechanical mixer. The mixer includes a central part having an internal cavity which forms an analysis chamber, a first end connected to the analysis head, and a plurality of stirring blades which are connected to a second end that is hollow so as to ensure fluid communication between the internal cavity and the liquid bath. The mechanical stirring blades are intended to be totally submerged, the central part comprises one or more openings intended to be partially submerged, and each (Continued)

mechanical stirring blade comprises at least one stirring flange oriented at a non-zero angle of orientation.

18 Claims, 2 Drawing Sheets

(56) References Cited

U.S. PATENT DOCUMENTS

2008/0083269 A1    4/2008  Sattmann
2017/0074800 A1*   3/2017  Benmansour .......... G01J 3/443

FOREIGN PATENT DOCUMENTS

EP    3023771 A1     5/2016
WO    2015177223 A1  11/2015

OTHER PUBLICATIONS

Written Opinion for PCT/FR2019/052594 dated Mar. 18, 2020 and English translation thereof.
Search Report for French application No. FR1860509 dated Jun. 28, 2019.
Rai, Awadhesh K. et al. "High temperature fiber optic laser-induced breakdown spectroscopy sensor for analysis of molten alloy constituents" In: Review of Scientific Instruments, Oct. 2002, vol. 73, No. 10, pp. 3589-3599.
Ramaseder, N, "Vai-Con Chem-A new continuous Chemical Analysis System of Liquid Steel in Mettallurgical Vessels" In: Nota Technica, Feb. 2004, pp. 60-63.
Darwiche, Sarah et al. "Impurity detection in solid and molten silicon by laser induced breakdown spectroscopy" In: Elsevier, Spectrochimica Acta Part B 74-75, 2012 pp. 115-118.

* cited by examiner

DEVICE FOR CHARACTERISING A LIQUID MATERIAL

CROSS-REFERENCE TO RELATED APPLICATIONS

This is a National Stage application of PCT international application PCT/FR2019/052594, filed on Nov. 4, 2019 which claims the priority of French Patent Application No. 1860509, filed Nov. 14, 2018.

TECHNICAL FIELD

The present invention pertains to the general field of the characterisation of a liquid material.

It relates to any technique for characterising a liquid material and surface analysis requiring a representative, stable and renewable analysis surface of the liquid. As examples, the invention may be used with spectrometry techniques such as the Inductively Coupled Plasma Mass Spectrometry (ICP-MS) technique and with other surface analysis techniques such as pyrometry. In a preferential manner, the invention is applied to the field of spectral analysis of a liquid material implementing a spectroscopy technique, and notably Laser Induced Breakdown Spectroscopy (LIBS).

The invention may be applied at high temperature or at room temperature. For example, it may be applied to materials at high temperature such as molten metals (aluminium, steel, zinc, sodium, etc.), molten salts, liquid glass in a vitrification furnace, and to liquids at low temperature such as water, oils, among others.

The invention may be used for different applications such as the purification of metals, water, oils, consumable liquid products, among others.

The invention is quite particularly concerned, but not exclusively, by the field of on-line spectral analysis by LIBS technique of molten metals, and specifically highly oxidisable molten metals, such as for example silicon, aluminium or zirconium. It may thus apply for example to the analysis of the chemical composition of molten liquid silicon during its purification by metallurgical methods, for its later use, for example in the photovoltaic industry.

The invention thus proposes a device for characterising at least one liquid material, an assembly comprising a vessel of at least one liquid material and such a characterisation device, as well as an associated characterisation method.

PRIOR ART

Within the context of the production of photovoltaic cells, silicon is the material the most widely used. It thus intervenes in the manufacture of so-called "crystalline" photovoltaic cells, that is to say which are based on silicon monocrystals or silicon polycrystals.

However, the presence of a high level of impurities in the liquid metallic silicon is harmful for the photoelectric effect because it favours the recombination of charge carriers, which influences their lifetime and thus the efficiency of the photovoltaic cells. Consequently, it is vital to be able to control the level of impurities in the silicon.

To obtain the silicon material with the purity required for its application, it is possible to use metallurgical methods (such as for example directional solidification, reactive evaporation, among others) in which the metallurgical silicon passes through a molten liquid phase, and is purified by exploitation of physical properties of the impurities of silicon (partition coefficients between liquid phase and solid or liquid phase, volatility properties, for example) or exploitation of reactivity properties of the impurities of silicon (plasma treatment, for example). However, in order to obtain silicon with the required purity, knowledge of the chemical composition of the molten metal and the kinetics of purification must be properly controlled and thus require a precise knowledge of the evolution of the concentrations of impurities in the material in the course of the treatment time.

In a normal manner, the analysis of the components of the silicon material in the course of its purification treatment is carried out by taking a sample, from the molten metal, using a container generally made of graphite in which the silicon is solidified, demoulded, then sent for analysis thereof. Nevertheless, this conventional procedure for analysing the material is not entirely satisfactory, and in particular is not suitable for the continuous control of the purity of the molten metal, because it requires prior steps of preparation of samples, which require time and have high costs.

Consequently, in view of these limitations, it has appeared desirable to be able to develop an in situ on-line tool for analysing the components of the silicon material, and liquid metals, so as to thereby reduce the analysis times, the costs and to ensure a continuous control of the chemical composition of the material over time. In this way, it is possible to have no need to sample the liquid metal melt and to provide information in real time on its composition.

To do so, in the perspective of the chemical analysis and the diagnostic of a given material, the laser constitutes a favoured tool because it makes it possible to carry out detection and identification operations in highly varied environment conditions. In addition, measurements carried out by laser technique have numerous advantages, and may enable in situ analysis, without either sampling or contact, as well as a rapidity of acquisition of information and use for local or remote analyses.

Among existing techniques using a laser, the laser induced breakdown spectroscopy (LIBS) technique constitutes a well-known physical analytical method, used for the analysis of the constituents of a material in order to characterise it, and represents one technology among the most promising for the on-line control of the composition of a molten metallic melt. The LIBS technique is typically used to enable rapid, direct and on-line analysis (without preparation of samples) of materials in solid, liquid or gaseous form. It thus implements laser ablation of a material to create a plasma, then the spectroscopic technique for the observation and the analysis of the light emission spectrum of the plasma in order to determine the components of the material.

More precisely, the LIBS technique involves focusing a laser pulse towards the surface of the material to analyse, which causes the formation of a micro-plasma. This micro-plasma forms virtually immediately, that is to say while the laser pulse is not terminated. At the end of the laser pulse, the atomic and ionic species of the micro-plasma de-excite and then re-emit a radiation that an analyser, i.e. a spectrometer, captures and translates in order to obtain a spectrum describing the chemical species that compose the material.

Thus, the LIBS technique can enable the identification, thanks to the emission wavelength, and the quantification, thanks to the emission intensity, of the components present in the material to analyse. In addition, since the LIBS technique makes it possible to carry out remote analysis, it proves to be particularly suited for the analysis of materials in the molten state at high temperature, and notably for the analysis of molten silicon, and the analysis of materials not being able to be handled because representing a potential hazard. Consequently, in the case of molten metals, such as silicon described previously, the LIBS technique is capable of providing in real time the evolution of the chemical composition of the material, and notably the impurities content of molten metallurgical silicon in the course of the different purification steps thereof.

Various solutions have thus already been envisaged in the prior art for developing the on-line analysis of molten metals by means of the LIBS technique.

Thus, in the article entitled "Impurity detection in solid and molten silicon by laser induced breakdown spectroscopy", Sarah Darwiche et al, 2012, Spectrochimica Acta Part B, Volume 74-75, pages 115-118, the authors disclose the basic principle consisting in focusing a laser pulse on the surface of a melt of molten metal, in particular silicon, and in collecting the signal emitted by the plasma generated by means of a detector. The optical measurement device and the laser are then placed at sufficient distance from the molten metal melt in order to avoid potential damage by the heat flux. Within the scope of this article, the analysis of molten silicon was carried out at a distance in a non-intrusive manner and on small quantities of material, in a medium made inert with argon. However, at larger scale, this measurement method may have a drawback linked to the fact that, in the case of molten metals, the chemical composition of the analysed surface is not generally representative of the composition of the overall volume of the metal. Indeed, due to the high reactivity of molten metals, and for example silicon, the material present at the interface with the atmosphere generally undergoes oxidation or nitridation phenomena which lead to the generation of surface slags. Due to the segregation of the various impurities between the molten metal and the oxidised phase, the slag generally does not have the same composition as the metal, which thus calls into question the reliability of measurements made with this method.

Alternative analysis systems have also been developed in order to create an analysis surface on the sample which is representative of the volume of molten metal. In the article entitled "High temperature fiber optic laser-induced breakdown spectroscopy sensor for analysis of molten alloy constituents", Awadhesh K. Rai et al, October 2002, Review of Scientific Instruments, Volume 73, pages 3589-3599, no 10, an analysis device by LIBS technique is described which makes it possible to approach the measurement head close to a molten aluminium melt and to create a free surface for the analysis using a spacer. The collection device is protected by a stainless steel shell. Nevertheless, this device is not satisfactory in that it notably has the drawback of limiting the analysis to materials with low melting points, typically of the order of 660° C. for aluminium at atmospheric pressure, whereas silicon, for example, has a melting point in the region of 1412° C. at atmospheric pressure.

The international application WO 02/063284 A2 further proposes another solution which provides circulating the liquid metal through a cell and carrying out the surface analysis thereof by LIBS technique by means of an optical access. This solution has been applied for zinc and aluminium, but it is not efficient for highly oxidisable metals such as silicon or zirconium. Indeed, in the case of a highly oxidisable metal, surface oxidation can occur with the residual oxygen of the load and make the analysis surface invalid.

The patent application US 2003/0234928 A1 for its part describes a complementary solution to the preceding, for very oxidisable metals. According to its principle, the end of a tube is dipped under the surface of the liquid metal through which a bubbling by inert gas is carried out to make it possible to renew the surface of the liquid metal and to generate an analysis volume in a neutral atmosphere. Optical information on the plasma is then collected by means of a set of mirrors and optic fibres. However, this solution has the major drawback of instability of the surface to analyse which is intimately linked to the dynamic of the generated bubble. A synchronisation, delicate to achieve, between the analysis frequency and the dynamic of formation of the bubble is then necessary. Moreover, the technical note entitled "VAI-CON® Chem-A New Continuous Chemical Analysis System of Liquid Steel in Metallurgical Vessels", N. Ramaseder et al, February 2004, La Metallurgia Italiana, pages 60-63, describes a similar solution within the context of the analysis of a steel melt. However, this solution has been tested on pilot furnaces and remains difficult to apply to industrial capacity furnaces because it uses a set of mirrors of which the adjustment is very specialised.

French patent application FR 3 021 407 A1 furthermore describes a device for analysing an oxidisable molten metal by LIBS technique provided with a stirring system making it possible to locally renew the surface of the molten metal and which is connected to a waveguide making it possible to focus the laser beam on the surface of the liquid. Thus, the device makes it possible to obtain rapid measurements, better detection limits and more robust analysis.

There exists however a need to further improve known devices for analysing molten metals by LIBS technique, and notably to have efficient stirring making it possible to obtain an analysis surface that is renewable, stable and representative of the metallic melt.

In the metallurgical industry, different shapes of mechanical stirring blades exist and have been designed for different applications. Indeed, certain blades are used to stir the melt and facilitate its purification while dissolving the metallic elements and while dispersing the gaseous particles therein.

As examples, the U.S. Pat. No. 4,717,540 A discloses a stirring system which makes it possible to facilitate the dissolution of the particles of nickel, of which the melting temperature is high, in a zinc melt and to avoid the formation of masses of semi-plastic nickel or the agglomeration of the zinc with these masses at the bottom of the melt. This stirring system is composed of a hollow rotating shaft which enables the introduction of an inert gas to the mixture by means of orifices. The system contains a grid of orifices which makes it possible to block the passage of non-dissolved nickel particles, introduced through a tube. The rotation speed retained is that which makes it possible to generate a vortex which is going to prevent the carrying out of any type of in situ surface analysis or control requiring measurement stability.

Moreover, U.S. Pat. No. 8,281,964 B2 describes the introduction of an inert gas, optionally with metal particles, into the liquid metal to eliminate hydrogen as well as oxide inclusions and at the same time to obtain rapid and efficient stirring. The gas reaches the liquid metal by passing through a hollow drive tube which passes through a rotating passage coupled to an off-centred motor and which is connected to the hollow rotating shaft by a clamp and a coupler. The system comprises a plate making it possible to regulate the flow of the aluminium melt during stirring, this plate playing the role of a chicane. The rotation parameters are chosen in such a way as to generate temporarily a vortex. The geometry of the blades has been designed in such a way as to rapidly well mix the gas with the metal in the chamber inside the blade which contains openings, inlet and outlet, and thus enable efficient degassing knowing that the speed of rotation may be reduced while keeping the same efficiency. This technique makes it possible to have efficient stirring and degassing. Nevertheless, the presence of the vortex is going to prevent the carrying out of in situ control measurements in the melt further to the absence of a stable analysis surface.

Furthermore, U.S. Pat. No. 4,802,656 A further teaches the design of blades making it possible to facilitate the dissolution of metal additives (Fe, Mg, Si, Mn, etc.) in the aluminium melt which make it possible to improve the properties of the aluminium, and notably the mechanical characteristics on the one hand. On the other hand, these blades make it possible to better disperse chlorine gas in the melt, by means of internal orifices, to eliminate the alkaline and alkaline-earth impurities which are behind the increase in the level of oxidation of the liquid metal or form compounds which can degrade their properties at high temperature. The problem resides in the retention of the gas which has a tendency to escape rapidly upwards to return to the atmosphere and the maintaining of the metals which, for their part, conversely, fall easily to the bottom of the melt and agglomerate. Unlike numerous blades used for high temperature applications, the geometry of the blade has here been designed to enable stirring to be obtained in the absence of turbulence and vortex zones, to have overall stirring of all the liquid of the melt, for the generation of efficient stirring with a low rotation speed, for a dissemination of the gas bubbles through the inner orifices to prevent them rising. However, the geometry of the blade serves to obtain efficient stirring at low rotation speed and does not guarantee the presence of an analysis zone that is stable, renewable and representative which could be intended to carry out in situ characterisation measurements.

Consequently, the different blades of the prior art make it possible to carry out stirring, to dissolve metal elements at the same time and to disperse gaseous particles. However, they are not intended to be used to guarantee the renewal, the reproducibility and the stability of a surface which may be analysed by an in situ characterisation technique such as for example the LIBS technique.

DESCRIPTION OF THE INVENTION

There consequently exists a need to propose an on-line device for characterising, notably by LIBS technique, liquid materials, notably oxidisable, and particularly highly oxidisable, molten metals comprising a stirring system enabling an analysis surface that is stationary, renewable and representative of the melt or the volume to be obtained, making it possible to simplify the analysis, reduce the analysis time, reduce the costs and ensure high quality monitoring of the materials. "Stationary surface" is taken to mean that the properties of the surface serving for the analysis are reproducible over time (namely notably its level, its shape, its composition, its flow speed, among others). In particular, the preparation and the renewal of the surface serving for the analysis must be able to ensure the evacuation of a third phase (slag, oxide, nitride, for example) which could invalidate the results of the analysis of the material.

The aim of the invention is thus to respond at least partially to the aforementioned need and to overcome the drawbacks relative to embodiments of the prior art.

The subject matter of the invention is thus, according to one of its aspects, a device for characterising, notably for analysing, at least one liquid material, notably a molten metal, in particular oxidisable, preferentially by spectroscopy technique, notably by LIBS technique, comprising:

means for characterisation, notably analysis by spectroscopy technique, notably by LIBS technique, rotating means for mechanically stirring a liquid melt of said at least one liquid material, the mechanical stirring means comprising:

a central part, extending along a longitudinal axis, intended to be positioned above the liquid melt of said at least one liquid material, comprising an inner cavity forming an analysis chamber delimited by a wall of the central part, the central part comprising a first end connected to the characterisation means, and a plurality of mechanical stirring blades, or further a plurality of mixing and/or stirring means, connected to a second end of the central part, opposite to the first end of the central part, the second end of the central part extending over a height along the longitudinal axis of the central part and being hollow so as to ensure fluidic communication between the inner cavity and the liquid melt of said at least one liquid material, the characterisation means being configured to enable the analysis of the surface of said at least one liquid material, situated in the portion directly in line with the inner cavity of the central part, characterised in that the mechanical stirring blades are intended to be totally immersed in the liquid melt of said at least one liquid material, in that the central part comprises one or more orifices formed in a traversal manner in its wall delimiting the inner cavity and situated above the second end of the central part bearing the mechanical stirring blades when the device is in place in the liquid melt of said at least one liquid material, the orifice or orifices being intended to be partially immersed according to a height in the liquid melt of said at least one liquid material, and in that each mechanical stirring blade comprises at least one stirring wing oriented according to a non-zero angle of orientation with respect to a transversal axis perpendicular to the longitudinal axis of the central part.

In a preferential manner, the device according to the invention enables the characterisation of at least one liquid material, and notably the analysis of at least one molten metal, notably oxidisable, and quite particularly by LIBS technique. However, the invention also applies to any technique for characterising at least one liquid material requiring in situ analysis and a need to carry out measurements on an analysis surface that is stable, representative and renewable of the liquid material. Thus, for example, the invention may use a mass spectrometry technique, such as the inductively coupled plasma mass spectrometry (ICP-MS) technique. This ICP-MS technique is capable of detecting metals and several non-metals at very low concentrations. The invention, coupled to different characterisation techniques such as the ICP-MS technique, may thus be used in several industrial applications such as the analysis of the contamination of water.

Thanks to the invention, it may thus be possible to improve further the on-line analysis of materials, and notably the on-line analysis by LIBS technique of molten metals, quite especially suited to oxidisable metals, and notably highly oxidisable metals, in comparison with the solutions of the prior art described previously. Indeed, the device according to the invention advantageously enables renewal of the surface to analyse by mechanical mixing using stirring blades, the stability of the analysis surface and the representativeness of the analysis surface. It also provides the presence of a specific analysis chamber to enable notably the focusing of the laser pulse used for example in the LIBS technique.

The device according to the invention may further comprise one or more of the following characteristics taken in isolation or according to all technically possible combinations thereof.

According to a first alternative, the mechanical stirring blades may extend, from the outer wall of the second end of the central part, while moving away from the inner cavity of the central part.

According to a second alternative, the mechanical stirring blades may extend, from the inner wall of the second end of the central part, inside the inner cavity of the central part.

Furthermore, the height of each mechanical stirring blade, along the longitudinal axis of the central part, may be substantially equal to the height, along the longitudinal axis of the central part, of the second end of the central part.

In addition, the angle of orientation may be less than or equal to 20°.

The mechanical stirring means may preferentially comprise three mechanical stirring blades and the central part may comprise three orifices separated from each other by longitudinal portions of wall.

The orifice or orifices may be intended to be partially immersed according to a height in the liquid melt of said at least one liquid material, at least equal to a quarter of the total height of the orifice or orifices.

Advantageously, the presence of such orifices on a portion of the central part situated above the mechanical stirring blades may make it possible to ensure the renewal of the surface to analyse. Indeed, the liquid material present in the portion directly in line with the inner cavity of the central part may see its level rise along the wall of the central part delimiting the inner cavity, in particular under the effect of centrifugation and capillarity. In this way, the presence of orifices enabling permanent flow out of the inner cavity of excess liquid material which rises along the wall, may make it possible to guarantee the renewal and the stabilisation of the level of the surface to analyse.

Furthermore, the central part may be in the form of a hollow tube (or shaft), notably in the form of a hollow cylindrical tube.

In particular, the second end of the central part, on which the mechanical stirring blades are fixed, is advantageously hollow so as to ensure vertical circulation of the liquid material.

The characterisation means may be comprised in an analysis head situated at the level of the first end of the central part. In addition, the mechanical stirring means may form together a mechanical mixer coupled to the analysis head.

The shape, the dimensions and/or the rotation speed of the mechanical stirring blades and/or the central part may be determined and adjusted as a function of the required stabilisation of the surface to analyse.

The dimensions of the mechanical stirring blades may be defined as a function of the dimensions of the vessel in which said at least one liquid material is situated.

In an advantageous manner, the central part may play the role of analysis chamber and enable the focusing of a laser pulse sent by the characterisation means in the form of analysis means by spectroscopy technique towards the surface to analyse, and to also enable the confinement of the micro-plasma that forms.

In a preferential manner, the central part may be made of graphite. In addition, the central part may be coated externally with a layer forming passivation barrier, notably vis-à-vis silicon, for example a layer of silicon carbide (SiC).

Moreover, the subject matter of the invention is further, according to another of its aspects, an assembly, characterised in that it comprises:
  a vessel comprising a melt of at least one liquid material, notably at least one molten metal, in particular oxidisable,
  a characterisation device such as defined previously, for the characterisation of said at least one liquid material of the vessel.

Said at least one liquid material may advantageously be a molten metal, notably a highly oxidisable metal, being notably selected from silicon or zirconium.

Said at least one liquid material may further be a high temperature material such as a molten metal, for example aluminium, steel, zinc, sodium, among others, a molten salt, a liquid glass in a vitrification furnace and/or a low temperature material such as water, an oil, among others.

The vessel may be of cylindrical shape having an inner diameter, the mechanical stirring blades may have a larger transversal dimension, notably a diameter, along a transversal axis perpendicular to the longitudinal axis of the central part. The following relationship may be verified:

$$0.2 < Dp/De < 0.7,$$

where:
Dp is the largest transversal dimension of the mechanical stirring blades, and
De is the inner diameter of the vessel.

The vessel may also be designated crucible. It may for example be made of graphite.

Furthermore, the assembly may also comprise means for heating the vessel comprising said at least one liquid material.

The vessel and the central part of the characterisation device may be preferentially made of a same material, notably graphite.

The flow regime of said at least one liquid material situated in the portion directly in line with the inner cavity of the central part is advantageously laminar, this flow being characterised by a Reynolds number Re comprised between 100 and 5000, and notably between 1000 and 2000, this Reynolds number Re being given by the following formula:

$$Re = [(\omega \times R) \times R']/v,$$

where:
  $(\omega \times R)$ represents the speed characteristic of the flow, namely the product of the angular rotation speed w of a mechanical stirring blade and the distance R between the end of the mechanical stirring blade and the axis of the central part,
  R' represents a dimension characteristic of the flow, namely notably the radius of the central part in the case where it is cylindrical or the side of the central part in the case where it is square for example, and
  v represents the kinematic viscosity of the liquid.

Thus, the choice of the value of the Reynolds number Re made to characterise the flow of said at least one liquid material situated in the portion directly in line with the inner cavity of the central part may thus have a direct impact on the parameters characterising the intensity of the mechanical stirring of the melt of liquid material.

Furthermore, the subject matter of the invention is also, according to another of its aspects, a method for characterisation, notably analysis, of at least one liquid material, notably at least one molten metal, in particular oxidisable, preferentially by spectroscopy technique, notably by LIBS technique, characterised in that it is implemented by means of a characterisation device such as defined previously, and in that it comprises the simultaneous steps consisting in:

carrying out a mechanical stirring of a liquid melt of said at least one liquid material by means of rotating mechanical stirring means of the device, analysing, notably by spectroscopy technique, the surface of said at least one liquid material situated in the portion directly in line with the inner cavity of the central part by means of characterisation means.

Said at least one liquid material may be an oxidisable molten metal, notably a highly oxidisable metal, being notably selected from silicon or zirconium, the characterisation means may be means for analysing by spectroscopy technique comprising means for analysing by LIBS technique, and the method may comprise at least one step of on-line analysis by LIBS technique of one or more impurities contained in said at least one oxidisable molten metal, notably silicon, during a process of purification of said at least one oxidisable molten metal.

The device, the assembly and the method according to the invention may comprise any one of the characteristics set out in the description, taken in isolation or according to all technically possible combinations with other characteristics.

BRIEF DESCRIPTION OF THE DRAWINGS

The invention will be able to be better understood on reading the detailed description that follows, of exemplary non-limiting embodiments thereof, and by examining the figures, schematic and partial, of the appended drawing, in which.

In all of these figures, identical references may designate identical or analogous elements.

In addition, the different parts represented in the figures are not necessarily according to a uniform scale, in order to make the figures more legible.

DETAILED DESCRIPTION OF PARTICULAR EMBODIMENTS

Figure 1:
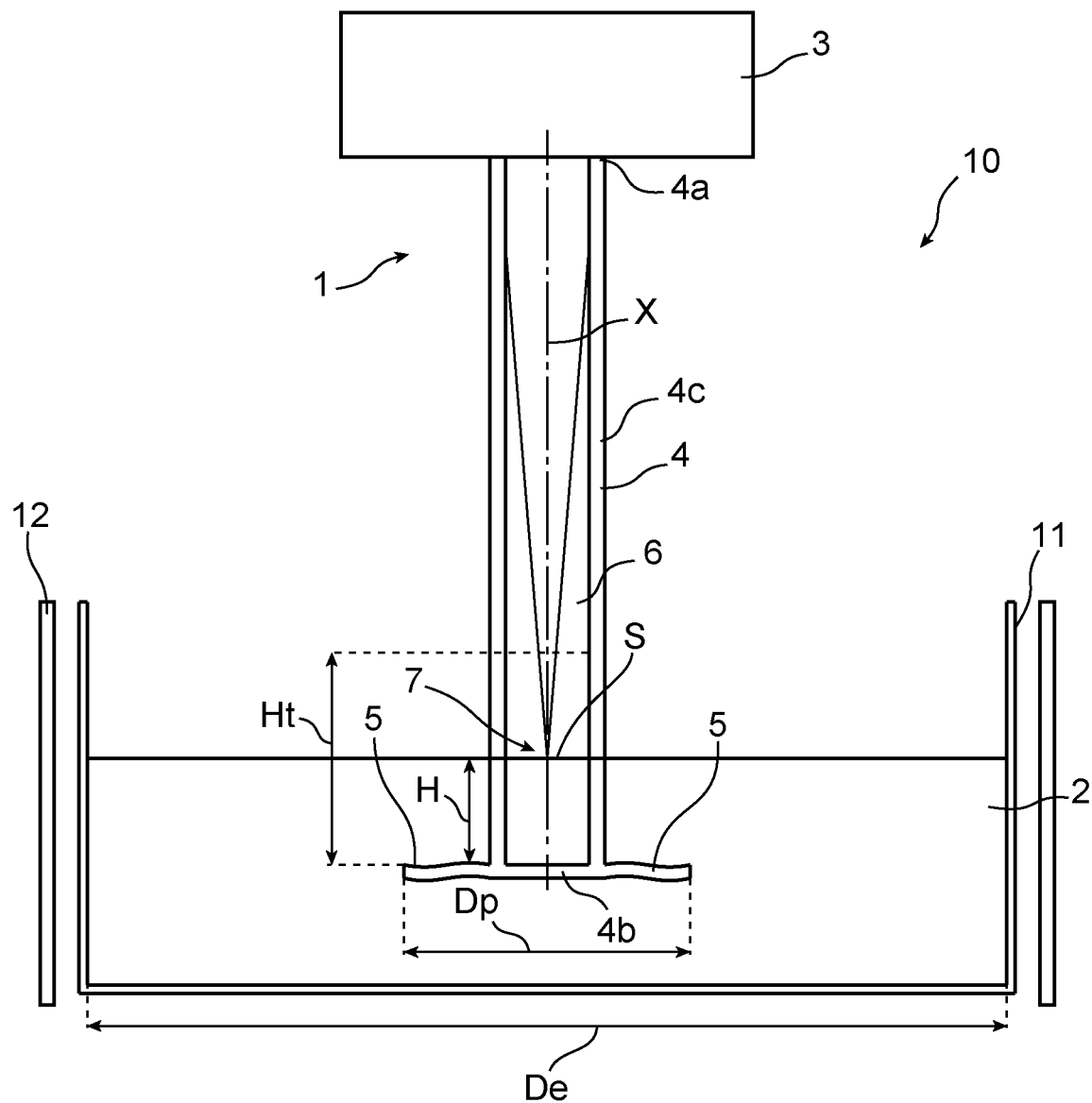
FIG. 1 represents, in section, an exemplary device for analysing an oxidisable molten metal by LIBS technique conforming to the invention.

In the example described hereafter with reference to FIG. 1, it is considered that the invention applies to the analysis of an oxidisable molten metal by LIBS technique. However, the invention could also apply to the analysis of a liquid material, for example water, by another spectroscopy technique, for example a mass spectrometry technique, such as the inductively coupled plasma mass spectrometry (ICP-MS) technique.

In addition, it is herein considered that the oxidisable molten metal 2 corresponds to silicon, and notably metallurgical silicon. The analysis device 1 according to the invention may then be used for the continuous control of the concentrations of impurities contained in this molten liquid silicon, during a process of purification of the metal aiming for example to enable later use for the production of photovoltaic cells. Obviously, this choice is in no way limiting. In particular, the invention could advantageously apply to other types of oxidisable molten metals, and notably highly oxidisable, such as for example zirconium, the surface analysis of which requires permanent renewal of the material in order to guarantee acceptable reliability of the measurement results.

Reference is thus made to FIG. 1 which represents, in section, an exemplary device 1 for analysing an oxidisable molten metal 2, namely silicon, by LIBS technique conforming to the invention.

In accordance with the invention, and as described in French patent application FR 3 021 407 A1, the analysis device 1 comprises means for analysing by LIBS technique 3 and rotating means for mechanically stirring 4, 5 a liquid melt of molten silicon 2. This liquid melt of silicon 2 comprises for example a load of upgraded metallurgical grade silicon (UMG-Si), which comprises a chemical composition of around 300 ppm by weight of metals taken together, around 15 ppm by weight of boron and around 20 ppm by weight of phosphorous.

More specifically, the analysis device 1 is used in an assembly 10 conforming to the invention which comprises, in addition to the analysis device 1, a vessel 11, commonly designated crucible, and for example made of silica and coated with silicon nitride, comprising the melt of molten liquid silicon 2. In particular, the use of the analysis device 1 according to the invention may be made in this example on an operation of segregation in a directional solidification furnace of a capacity of around 60 kg. Moreover, in order to enable the heating of the silicon 2 in the vessel 11 and the maintaining of a temperature above its melting temperature of around 1412° C. at atmospheric pressure, resistive heating means 12 of the vessel 11 are also provided. In this way, the load of silicon 2 may for example be melted under a flow of argon by resistive heating.

Furthermore, the mechanical stirring means 4, 5 form together a mechanical mixer 4, 5, coupled to the analysis means by LIBS technique 3 situated in a LIBS analysis head 3.

This mechanical mixer 4, 5 comprises a central part 4 partially immersed in the liquid melt of molten silicon 2, which comprises an inner cavity 6 forming an analysis chamber. In addition, the central part 4 comprises a first end 4a which is connected to the LIBS analysis head 3.

The central part 4 is for example in the form of a cylindrical hollow stirring tube, provided with an annular wall 4c delimiting the inner cavity 6, and has for example an inner diameter of around 25 mm and an outer diameter of around 65 mm.

The central part 4 plays the role of analysis chamber and enables the focusing of the laser pulse sent by the LIBS analysis head 3 towards the surface S to analyse of the silicon melt 2. This central part 4 is notably made of graphite, and externally coated with a layer forming passivation barrier vis-à-vis silicon, for example a layer of silicon carbide.

Figure 2:
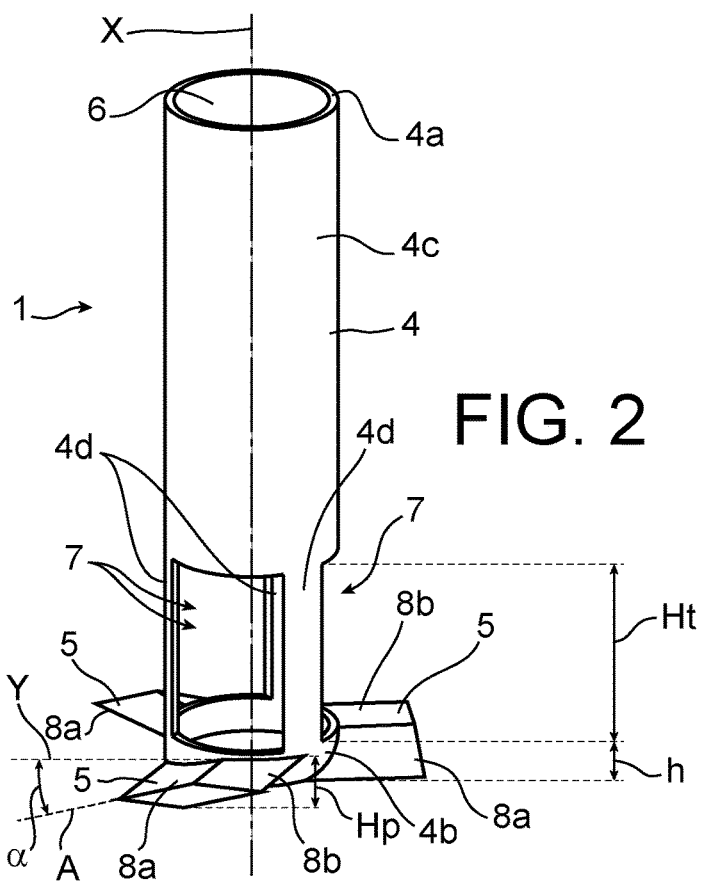
FIGS. 2 and 3 represent, partially and in perspective, two exemplary embodiments of the central part and mechanical stirring blades of a device for analysing an oxidisable molten metal by LIBS technique conforming to the invention.
Figure 3:
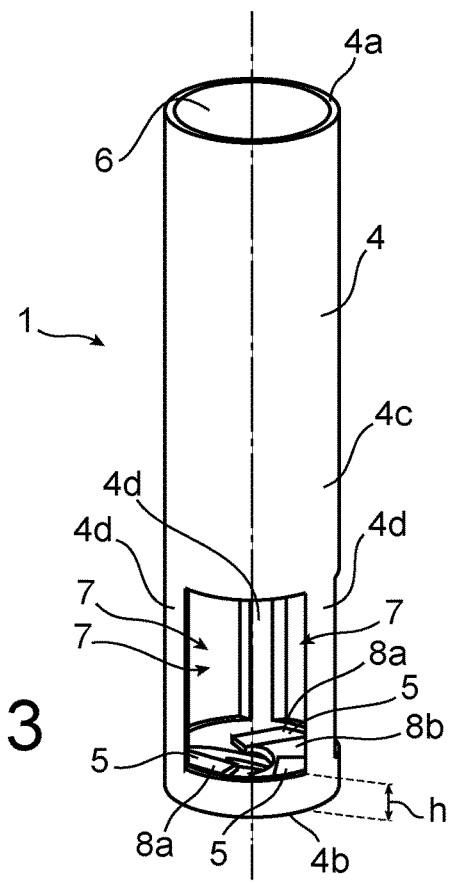

In addition, the mechanical mixer 4, 5 also comprises mechanical stirring blades 5 totally immersed in the silicon melt 2, and connected to a second end 4b of the central part 4, advantageously hollow so as to ensure fluidic communication between the inner cavity 6 and the silicon melt 2. The mechanical stirring blades 5 may be produced in different ways, their representation being very schematic in FIG. 1. FIGS. 2 and 3, described hereafter, make it possible to envisage two distinct embodiments of the blades 5.

Furthermore, the central part 4 comprises orifices 7 formed in its annular wall 4c, more clearly visible in FIGS. 2 and 3, which are situated above the mechanical stirring blades 5 when the device 1 is in place in the liquid silicon melt 2. These orifices 7 make it possible to ensure the renewal of the surface S to analyse and to maintain the level of silicon 2 at a constant level in the inner cavity 6. A height H of these orifices 7 is totally immersed in the liquid silicon melt 2, which implies total immersion of the mechanical stirring blades 5.

Thus, the orifices 7 of the central part 4 are partially immersed in the liquid silicon melt 2, by a height H, and they have sufficient width to ensure a horizontal circulation of liquid silicon 2 and not uniquely an evacuation of the excess of metal.

When the silicon 2 is completely molten, the central part 4 is introduced progressively into the silicon melt 2 with total immersion of the stirring blades 5, then thanks to a motor, it is rotated to ensure the stirring of the silicon melt 2. The analysis by LIBS technique is then carried out on the surface S of the silicon 2 situated in the portion directly in line with the central part 4.

The rotation of the central part 4 may for example be achieved using at least two pinions fixed around the central axis X, or longitudinal axis, of the central part 4. The speed of rotation of the mechanical mixer 4, 5 may be fixed so as to obtain laminar flow of the silicon 2 directly in line with the central part 4, and facilitated circulation of the silicon 2 through orifices 7 provided on the central part 4.

In a more general manner, it is advantageous to obtain a flow regime of the silicon 2 situated directly in line with the inner cavity 6 of the central part 4 that is laminar. Laminar flow is desired in the hollow part of the blade up to the analysis surface which must be stable, without turbulence. Outside of this zone, efficient stirring is desired and it is possible that the flow is not laminar.

To do so, the Reynolds number Re is preferentially comprised between 100 and 5000, and notably between 1000 and 2000, this Reynolds number Re being given by the following formula: Re=[(ω×R)×R']/v, in which: (ω× R) represents the characteristic speed of the flow, namely the product of the angular speed of rotation ω of a mechanical stirring blade 5 and the distance R between the end of the mechanical stirring blade 5 and the axis X of the central part 4, R' represents a characteristic dimension of the flow, namely the radius of the central part 4, and v represents the kinematic viscosity of the liquid.

The renewal of the analysis surface S, targeted by the laser traversing the hollow central part 4 connected to the LIBS analysis head 3, is guaranteed by the use of orifices 7 at the level of the central part 4. These orifices 7 have a height H which is totally immersed in the liquid silicon melt 2, which leads to total immersion of the stirring blades 5.

The second end 4b of the central part 4, on which the stirring blades 5 are fixed, is advantageously hollow to be able to ensure vertical circulation of the liquid metal 2 upwards and more precisely towards the surface to analyse S targeted by the laser of the LIBS head 3. The diameter of this second end 4b may vary as a function of the diameter of the vessel 11 containing the liquid silicon 2. Furthermore, the height h of the second end 4b, visible in FIGS. 2 and 3, is of the order of 6 mm.

The stability of the analysis surface S is obtained by stirring at moderate rotation speeds which avoids the formation of a vortex or turbulence zones or cavities.

The analysis surface S is representative given that the stirring is efficient and enables circulation of the liquid silicon 2 in the melt assembly. The efficiency of the stirring is obtained by means of stirring parameters, such as speed and direction of rotation, positioning of the blades 5, among others, and by means of the shape of the stirring blades 5. These blades may be arranged inside the second end 4b, as described hereafter with reference to FIG. 3, or outside, as described hereafter with reference to FIG. 2.

FIGS. 2 and 3 represent, partially and in perspective, two exemplary embodiments of the central part 4 (the LIBS analysis head 3 not being represented) and mechanical stirring blades 5 of a device for analysing 1 molten silicon 2 by LIBS technique.

The exemplary embodiment of FIG. 2 is characterised in that the mechanical stirring blades 5 extend, from the outer wall of the second end 4b of the central part 4, while moving away from the inner cavity 6 of the central part 4. They are thus here external stirring blades 5.

Conversely, the exemplary embodiment of FIG. 3 is characterised in that the mechanical stirring blades 5 extend, from the inner wall of the second end 4b of the central part 4, inside the inner cavity 6 of the central part 4. They are thus here internal stirring blades 5.

However, in a manner common to the two embodiments and in accordance with the invention, the stirring blades 5 are intended to be totally immersed in the silicon melt 2, as visible in FIG. 1.

Furthermore, without this being limiting, each device 1 comprises three mechanical stirring blades 5 and the central part 4 comprises three orifices 7 separated by three longitudinal portions of wall 4d, put in place in a symmetrical manner by circular repetition and at constant distance. The number of blades 5 may vary as a function of the stirring speed and the nature of the liquid to stir.

In the present case, the speed of rotation of the blades 5 depends on the shape of the blades 5 and on the aim to attain, and may for example be comprised between 20 and 25 rpm.

The height of introduction in the silicon melt 2 advantageously corresponds to a sufficient height to ensure the rising of the liquid drawn up by the hollow central second end 4b towards the free analysis surface S. Thus, the total height Ht of the orifices 7, visible in FIGS. 1 and 2, may be of the order of 40 mm, and the immersed height H of the orifices 7, visible in FIG. 1, is for example of the order of 10 mm.

Furthermore, as may be seen in FIG. 1, the vessel 11 is of cylindrical shape and has an inner diameter De, and the mechanical stirring blades 5 have a larger transversal dimension assimilable to a diameter Dp, along the transversal axis Y perpendicular to the longitudinal axis X of the central part 4, of the order of several centimetres up to ten or so metres. These parameters De and Dp verify the following relationship: 0.2<Dp/De<0.7.

According to the two embodiments of FIGS. 2 and 3, each mechanical stirring blade 5 comprises a first stirring wing 8a oriented according to an angle of orientation a which is of the order of 20° with respect to the transversal axis Y perpendicular to the longitudinal axis X of the central part 4, as visible in FIG. 2.

Each stirring blade 5 also comprises a second stirring wing 8b, connected to the first stirring wing 8a, and having a smaller inclination than that of the first stirring wing 8a with respect to the transversal axis Y. The first stirring wing 8a comprises the leading edge of the corresponding stirring blade 5.

Overall, the shape of each stirring blade 5 is thus slightly inclined with respect to the horizontal in such a way that the upper part of the blade 5 and the lower part of the blade 5 are substantially at the same level as the second end 4b. Put another way again, as visible in FIG. 2 for example, the height Hp of each mechanical stirring blade 5 is substantially equal to the height h of the second end 4b of the central part 4. The invention thus proposes here a small inclination of the blades 5 unlike solutions of the prior art for which the angle of inclination is much more important and imposes having a contact surface with the liquid which is larger and consequently requires more energy to be displaced.

Here, the inclination of the first stirring wing 8a forming the leading edge imposes a vertical displacement of the liquid which enters into contact with this leading edge.

According to the first embodiment of FIG. 2, the external blades 5 make it possible to generate an axial flow, i.e. a vertical movement of the liquid, at the level of the blades 5 outside of the central part 4. The direction of this movement, downwards or upwards, is linked to the direction of rotation. The second hollow end 4b enables a sucking upwards of the liquid, i.e. towards the analysis surface S, and its evacuation by means of orifices 7.

According to the second embodiment of FIG. 3, the inner blades 5 enable, for a rotation in the clockwise direction, the sucking of the liquid through the second hollow end 4b upwards and more precisely towards the free analysis surface S and next its evacuation by means of orifices 7. The flow speed remains constant during stirring.

Unlike blades of the prior art, the behaviour of the liquid generated by the two shapes of blades of the embodiments of FIGS. 2 and 3 is advantageous and original. In addition to the stirring of the liquid, the second hollow end 4b allows a vertical sucking up of the liquid which is evacuated by means of orifices 7 and thus renews the analysis surface S.

The number of blades 5 may vary as a function of the desired power and stirring speed, the properties of the liquid and the geometry of the vessel 11.

The direction of rotation is imposed by the shape of the blades 5, and more precisely the wings 8a, 8b.

Tests were carried out in a vessel 11 in the form of a transparent crucible using dimensions similar to those of the graphite crucible in which silicon, typically 3 kg, is melted in the melting furnace. The outer diameter of this crucible 11 is around 125 mm and the inner diameter is around 115 mm with an outer height of around 240 mm and an inner height of around 228 mm.

The tests were carried out in water given that the physical properties of water at 20° C. come close to those of liquid silicon at 1450° C.

The monitoring of the flow of water was obtained by using tracers in suspension in the fluid. These tracers locally follow the movement of the liquid.

In the case of internal stirring blades 5, as in the exemplary embodiment of FIG. 3, the rotation of the blades in the clockwise direction brings about contact between the particles of water with the leading edge of the inclined blades. This edge corresponds to the lower part of the blade, behind a sliding of the particles of the liquid through the blade upwards leading to a vacuum on the other side of the blade which is filled by the lower liquid. In other words, a sucking up of the liquid found at the bottom of the blade 5 is induced towards the free surface S. The presence of the orifices 7 enables horizontal evacuation of the particles that reach the free surface S until reaching the edges then descending along the wall of the vessel 11 to return to the centre thereof by means of an axial movement. The free surface S targeted by the laser thus remains stable, renewable and representative with an absence of vortex, turbulence zone or cavity.

In the case of external stirring blades 5, as in the exemplary embodiment of FIG. 2, the stirring induced by the blades rotating in an anticlockwise direction is characterised by an important sucking up movement below the blades 5 which induces a rise of a large quantity of particles upwards by means of the hollows of the second end 4b. At the level of the ends of the blades 5, the particles which are in contact with the leading edge have a tendency to descend while sliding on the blade, which generates a movement in the form of an axial loop at the level of the blades 5 and forces the fluid to rise by means of the second end 4b of the central part 4 towards the free surface S and thus the renewal of the analysis surface S. The flow through the second end 4b is with a Reynolds number of Re=1277, which corresponds to laminar flow.

When completely molten, the blades 5, made for example of graphite, bonded to the central part 4 made of alumina, with for example an inner diameter of 14 mm and an outer diameter of 18 mm, are progressively introduced into the silicon melt 2, namely a total introduction of the blades 5 and partial introduction of the orifices 7 according to a translational movement, using welded cup bellows. Then, thanks to a hollow rotating passage connected to an off-centred motor, the central part 4 is made to rotate to ensure the stirring of the melt. To avoid any deviation of the central axis X during rotation which could damage the shaft, a centring system is used. The speed of rotation of the stirring device 1 is set at 25 rpm. These conditions enable laminar flow and circulation of the liquid through orifices 7 provided in the tube 4. This rotation system is connected to the LIBS head 3 without the rotation of the connecting clamp. The LIBS measurement chain is for example composed of a Nd-YAG nano pulsed laser (pulse duration of 5 ns) operating at a wavelength of 1064 nm. The laser makes it possible to deliver pulses of a maximum energy of 200 mJ. The signal is recovered by means of a detector then focused at the input of a monochromator using a bundle of optic fibres.

Obviously, the invention is not limited to the exemplary embodiments that have just been described. Various modifications may be made thereto by those skilled in the art.

The geometry of the stirring blades 5, for example the diameter, the inclination of the wings, the number of wings, the dimensions of the orifices 7, the number of orifices 7, the shape of the orifices 7 and the stirring parameters, such as speed of rotation, height of introduction of the blades 5, direction of rotation, will be able to be adapted as a function of the nature of the material to analyse and the geometry of the vessel 11.

The invention may further be used for different liquids, such as water, liquid metals, among others, and at different temperatures, notably room temperature or high temperatures.

The blades 5 may be made of graphite or based on any material that can withstand the environment to which they are subjected. For example, if the blades 5 are used at high temperatures, this material must have good refractoriness as a function of the temperature of the melt, good resistance to thermal shocks given that the blades are introduced then removed from the melt several times and good resistance to abrasion and erosion as a function of the nature of the liquid. At room temperature, the blades 5 may be made for example of polyamide.

For applications at high temperatures, the central part 4 may be made of a material which must, in addition to its resistance to the thermomechanical stresses of the environment, be thermally insulating in order not to damage the LIBS analysis means. For example, the central part 4 may be made of alumina.

The link between the central part 4 and the blades 5 may be achieved by bonding, threading and/or screw thread.

Furthermore, the LIBS analysis means may comprise a laser able to generate a laser pulse towards the surface to analyse of the silicon melt 2, a set of mirrors enabling the focusing of the laser pulse towards the surface to analyse, a device for collecting the emission of the micro-plasma formed by the laser pulse connected to an optic fibre, and an emission spectrometer enabling the analysis of the collected emissions.

The duration of the laser pulse may be of the order of the femtosecond to the nanosecond. In addition, the laser can operate at different wavelengths, for example comprised between 266 nm and 1064 nm, and preferentially in the infrared domain. Its energy may be greater than 100 mJ.

The set of mirrors may enable the focusing of the laser pulse towards the surface to analyse at a distance of around 2 m.

The focusing of the laser pulse towards the surface to analyse may enable the creation of the micro-plasma, the emissions of which are collected. The emission spectrometer, which makes it possible to analyse the collected emissions, may for example be a monochromator of the "Czerny-Turner" type, provided with suitable diffraction gratings.

Moreover, the analysis device 1 according to the invention may comprise a system for blowing inert gas, notably helium or argon, through the central part 4.

In an advantageous manner, the blowing of inert gas inside the central part 4 may make it possible to avoid potential contaminations of the surface to analyse, for example avoid oxidation in the event of micro-leakages. Moreover, the blowing of inert gas may also have the advantage of increasing the measurement sensitivity and decreasing the detection limits of the analysis by the spectroscopy technique.

What is claimed is:

1. A device for characterising at least one liquid material, comprising:
   characterisation means,
   rotating means for mechanically stirring a liquid melt of said at least one liquid material, the rotating means comprising:
      a central part extending along a longitudinal axis and configured to be positioned above the liquid melt of said at least one liquid material, the central part comprising a wall, an inner cavity delimited by the wall and forming an analysis chamber, and a first end connected to the characterisation means, and
      a plurality of mechanical stirring blades connected to a second end of the central part, opposite to the first end of the central part, the second end of the central part extending over a height along the longitudinal axis of the central part and being hollow so as to ensure fluidic communication between the inner cavity and the liquid melt of said at least one liquid material,
   wherein the characterisation means is configured to enable the analysis of the surface of said at least one liquid material, situated in the portion directly in line with the inner cavity of the central part,
   wherein the mechanical stirring blades are configured to be totally immersed in the liquid melt of said at least one liquid material,
   wherein the central part comprises one or more orifices formed in a traversal manner in the wall and configured to be situated above the second end of the central part bearing the mechanical stirring blades when the device is in place in the liquid melt of said at least one liquid material, the orifice or orifices being configured to be partially immersed according to a height in the liquid melt of said at least one liquid material, and
   wherein each mechanical stirring blade comprises at least one stirring wing oriented according to a non-zero angle of orientation with respect to a transversal axis perpendicular to the longitudinal axis of the central part.

2. The device according to claim 1, wherein the device is configured for the analysis of at least one oxidisable molten metal by LIBS technique, the characterisation means being means for analysing by spectroscopy technique comprising means for analysing by LIBS technique.

3. The device according to claim 1, wherein the mechanical stirring blades extend from the outer wall of the second end of the central part, while moving away from the inner cavity of the central part.

4. The device according to claim 1, wherein the mechanical stirring blades extend from the inner wall of the second end of the central part, inside the inner cavity of the central part.

5. The device according to claim 1, wherein a height of each mechanical stirring blade along the longitudinal axis of the central part is substantially equal to the height of the second end of the central part.

6. The device according to claim 1, wherein the angle of orientation is less than or equal to 20°.

7. The device according to claim 1, wherein the rotating means comprise three mechanical stirring blades and wherein the central part comprises three orifices separated from each other by longitudinal wall portions.

8. The device according to claim 1, wherein the height in which the orifice or orifices are configured to be partially immersed in the liquid melt of said at least one liquid material is at least equal to a quarter of the total height of the orifice or orifices.

9. The device according to claim 1, wherein the central part is in the form of a hollow cylindrical tube.

10. An assembly comprising:
    the device according to claim 1, and
    a vessel comprising the liquid melt of said at least one liquid material.

11. The assembly according to claim 10, wherein said at least one liquid material is a molten metal.

12. The assembly according to claim 10, wherein the vessel and the central part of the device are made of a same material.

13. The assembly according to claim 10, wherein the vessel is of cylindrical shape having an inner diameter, wherein the mechanical stirring blades have a transversal dimension along the transversal axis that is larger than the inner diameter, and wherein the following relationship is verified:

$$0.2 < Dp/De < 0.7,$$

where:
Dp is a largest transversal dimension of the mechanical stirring blades, and
De is the inner diameter of the vessel.

14. A method of using the device according to claim 1 for characterising said at least one liquid material, and the method comprising simultaneous steps consisting of:
    carrying out a mechanical stirring of the liquid melt of said at least one liquid material by the rotating means of the device, and
    analysing the surface of said at least one liquid material situated directly in line with the inner cavity of the central part using the characterisation means.

15. The method according to claim 14, wherein said at least one liquid material is an oxidisable molten metal, the characterisation means are means for analysing by spectroscopy technique comprising means for analysing by LIBS technique, and the method comprises at least one step of on-line analysis by LIBS technique of one or more impurities contained in said at least one oxidisable molten metal, during a process of purification of said at least one oxidisable molten metal.

16. The device according to claim 1, wherein the orifice or orifices are configured to be partially immersed in the liquid melt such that a surface of the liquid melt outside of the central part is level with the orifice or orifices.

17. A method of using the device according to claim 1 for characterising said at least one liquid material, and the method comprising:
   arranging said rotating means such that the mechanical stirring blades are totally immersed in the liquid melt of said at least one liquid material, and the orifice or orifices are partially immersed in the liquid melt of said at least one liquid material, and
   analysing the surface of said at least one liquid material using the characterisation means.

18. The method according to claim 17, wherein the orifice or orifices are partially immersed in the liquid melt such that a surface of the liquid melt outside of the central part is level with the orifice or orifices.

* * * * *